United States Patent
Peretz et al.

(10) Patent No.: US 10,278,657 B2
(45) Date of Patent: May 7, 2019

(54) METHOD AND SYSTEM FOR PERFORMING AN IMAGING SCAN OF A SUBJECT

(71) Applicant: General Electric Company, Schenectady, NY (US)

(72) Inventors: Aharon Peretz, Tirat Carmel (IL); Yaron Hefetz, Kibutz Alonim (IL); Lana Volokh, Haifa (IL)

(73) Assignee: General Electric Company, Schenectady, NY (US)

( * ) Notice: Subject to any disclaimer, the term of this patent is extended or adjusted under 35 U.S.C. 154(b) by 25 days.

(21) Appl. No.: 15/615,446

(22) Filed: Jun. 6, 2017

(65) Prior Publication Data

US 2017/0273644 A1 Sep. 28, 2017

Related U.S. Application Data

(62) Division of application No. 13/487,901, filed on Jun. 4, 2012.

(51) Int. Cl.
*A61B 6/03* (2006.01)
*A61B 6/00* (2006.01)
*H04N 7/18* (2006.01)

(52) U.S. Cl.
CPC .............. *A61B 6/037* (2013.01); *A61B 6/503* (2013.01); *H04N 7/18* (2013.01)

(58) Field of Classification Search
CPC ............ H04N 7/18; A61B 6/037; A61B 6/503
See application file for complete search history.

(56) References Cited

U.S. PATENT DOCUMENTS

| | | | |
|---|---|---|---|
| 5,757,006 A | 5/1998 | DeVito et al. |
| 6,242,743 B1 | 6/2001 | DeVito et al. |
| 6,271,524 B1 | 8/2001 | Wainer et al. |
| 6,696,686 B1 | 2/2004 | Wainer et al. |
| 6,946,660 B2 | 9/2005 | El-Hanany et al. |
| 6,956,925 B1 | 10/2005 | Hoffman |
| 7,166,848 B2 | 1/2007 | El-Hanany et al. |
| 7,208,740 B2 | 4/2007 | El-Hanany et al. |
| 7,326,906 B2 | 2/2008 | Shalom et al. |
| 7,339,176 B2 | 3/2008 | El-Hanany et al. |
| 2005/0129295 A1 | 6/2005 | Shanmugam et al. |

(Continued)

OTHER PUBLICATIONS

United States Statutory Invention Registration, Reg. No. H12, Published: Jan. 7, 1986, Inventors: Bennett et al, Asignee: The United States of America as represented by the United State Department of Energy, Washington, DC, (13 pages).

(Continued)

*Primary Examiner* — Mark D Remaly
(74) *Attorney, Agent, or Firm* — Dean D. Small; The Small Patent Law Group, LLC

(57) ABSTRACT

A method for performing an imaging scan of a subject includes positioning a narrow field-of-view camera at a first imaging position to acquire a first set of imaging information of a first object of interest, positioning the narrow field-of-view camera at a second imaging position to acquire a second set of imaging information of a second object of interest, determining emission counts for the first and second sets of imaging information, and utilizing the determined emission counts to generate a value that indicates a probability of a successful medical procedure being performed on the subject.

18 Claims, 10 Drawing Sheets

(56) References Cited

U.S. PATENT DOCUMENTS

| | | |
|---|---|---|
| 2005/0218331 A1 | 10/2005 | Blevis et al. |
| 2005/0242292 A1 | 11/2005 | El-Hanany et al. |
| 2006/0011852 A1 | 1/2006 | El-Hanany et al. |
| 2007/0040126 A1 | 2/2007 | El-Hanany et al. |
| 2007/0232881 A1 | 10/2007 | Shalom et al. |
| 2007/0278387 A1 | 12/2007 | Shalom et al. |
| 2007/0295914 A1 | 12/2007 | El-Hanany et al. |
| 2008/0149842 A1 | 6/2008 | El-Hanany et al. |
| 2008/0237482 A1 | 10/2008 | Shahar et al. |
| 2008/0277591 A1 | 11/2008 | Shahar et al. |
| 2009/0238756 A1* | 9/2009 | Yang .................. A61K 31/165 424/1.65 |
| 2011/0110570 A1* | 5/2011 | Bar-Shalev ........... G06T 11/005 382/131 |
| 2011/0152679 A1* | 6/2011 | Morag ................. A61B 6/037 600/431 |

OTHER PUBLICATIONS

Currie et al., "Risk Satisfaction in Heart Failure Using 123I-MIBG", Journal of Nuclear Medicine Technology, 2011; 39:295-301, Published Online: Oct. 3, 2011, DOI: 10.2967/jnmt,11,088369 (8 pages).

Kelesidis et al., "Use of Cardiac Radionuclide Imaging to Identify Patients at Risk for Arrhythmic Sudden Cardiac Death", Journal of Nuclear Cardiology, Jan./Feb. 2012, vol. 19, No. 1; 142-52 (11 pages).

* cited by examiner ure scan of a subject is provided. The method includes positioning a narrow field-of-view camera at a first imaging position to acquire a first set of imaging information of a first object of interest, positioning the narrow field-of-view camera at a second imaging position to acquire a second set of imaging information of a second object of interest, determining emission counts for the first and second sets of imaging information, and utilizing the determined emission counts to generate a value that indicates a probability of a successful medical procedure being performed on the subject.
METHOD AND SYSTEM FOR PERFORMING AN IMAGING SCAN OF A SUBJECT

RELATED APPLICATIONS

The present application is a divisional application of and claims priority to U.S. patent application Ser. No. 13/487,901, "Method And System For Performing An Imaging Scan Of A Subject," filed Jun. 4, 2012, the subject matter of which is hereby incorporated by reference in its entirety.

BACKGROUND OF THE INVENTION

The subject matter disclosed herein relates generally to nuclear medicine (NM) imaging systems, and more particularly, to a methods and systems for performing an imaging scan of a subject.

In NM imaging, radiopharmaceuticals are injected into a person and then detectors (e.g., gamma cameras), typically mounted on a gantry, capture and form images from the radiation emitted by the radiopharmaceuticals. The NM images primarily show physiological function of, for example, a patient or a portion of a patient being imaged.

Collimation may be used to create an image of radiation-emitting objects in the field of view of the detectors. Different types of collimation are known, for example, different shapes and configurations of collimators are known for use in different types of applications. However, when designing collimators a tradeoff exists between resolution and sensitivity. For example, a high-resolution collimator views a very narrow column of activity from the patient, and therefore provides high spatial resolution, but at a reduced sensitivity. In contrast, a high sensitivity collimator accepts radiation from a wider range of angles, which increases the sensitivity, but reduces resolution. Thus, depending on desired or required imaging characteristics or properties, collimators are designed to provide resolution and sensitivity levels to maximize or optimize imaging based on the desired or required characteristics or properties. However, such designs may perform unsatisfactorily in different applications.

As one example, in pinhole collimators, such as for Single Photon Emission Computed Tomography (SPECT) imaging detectors, the field of view of the detector depends on the size of the detector and the focal length of the collimator. Thus, there is a tradeoff between field of view, resolution, sensitivity, and detector area.

Accordingly, known collimator designs often require one or more compromises. Thus, these designs may result in detectors that have less than optimal imaging for a particular application.

BRIEF DESCRIPTION OF THE INVENTION

In one embodiment, a method for performing an imaging scan of a subject is provided. The method includes positioning a narrow field-of-view camera at a first imaging position to acquire a first set of imaging information of a first object of interest, positioning the narrow field-of-view camera at a second imaging position to acquire a second set of imaging information of a second object of interest, determining emission counts for the first and second sets of imaging information, and utilizing the determined emission counts to generate a value that indicates a probability of a successful medical procedure being performed on the subject.

In another embodiment, a medical imaging system is provided. The medical imaging system includes a narrow field of view camera, a table, and a processor configured to acquire a first set of imaging information of a first object of interest while the narrow field-of-view camera is positioned at a first imaging position, acquire a second set of imaging information of a second object of interest while the narrow field-of-view camera is positioned at a second imaging position, determine emission counts for the first and second sets of imaging information, and utilize the determined emission counts to generate a value that indicates a probability of a successful medical procedure being performed on the subject.

In a further embodiment, a non-transitory computer readable medium is provided. The non-transitory computer readable medium is encoded with a program programmed to instruct a computer to acquire a first set of imaging information of a first object of interest using a narrow field-of-view camera positioned at a first imaging position, acquire a second set of imaging information of a second object of interest using the narrow field-of-view camera positioned at a second imaging position, determine emission counts for the first and second sets of imaging information, and utilize the determined emission counts to generate a value that indicates a probability of a successful medical procedure being performed on the subject.

DETAILED DESCRIPTION OF THE INVENTION

Figure 1:
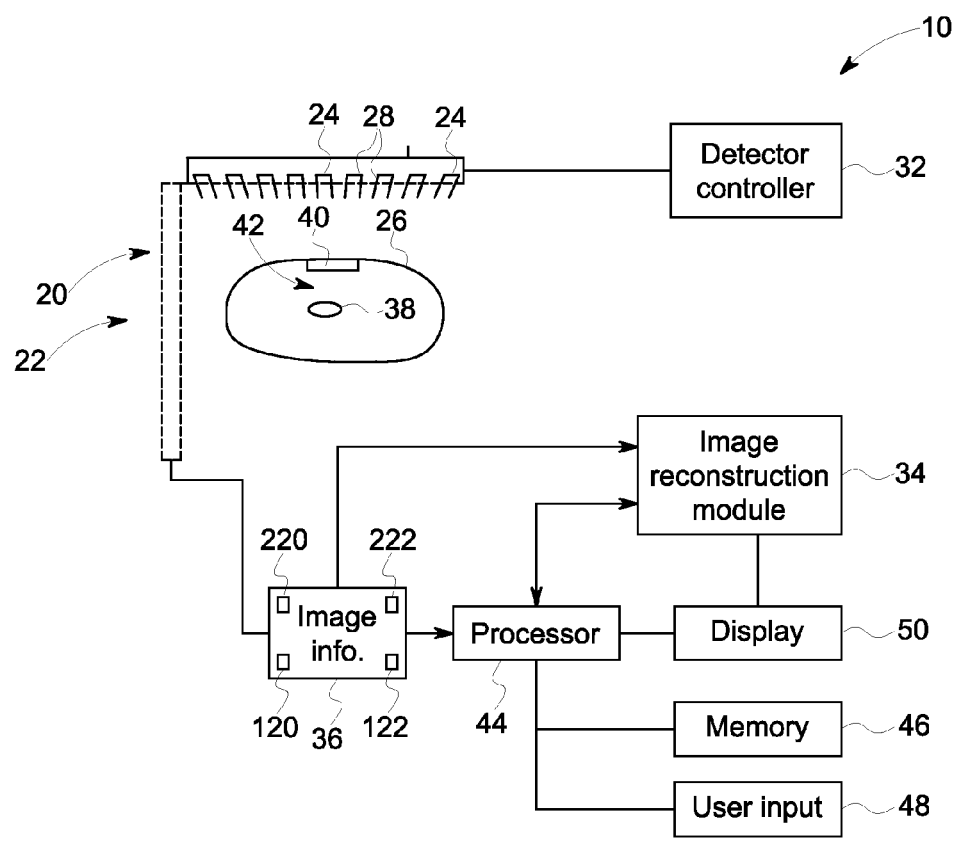
FIG. 1 is a simplified block schematic diagram of an imaging system formed in accordance with various embodiments.

The foregoing summary, as well as the following detailed description of various embodiments, will be better understood when read in conjunction with the appended drawings. To the extent that the figures illustrate diagrams of the functional blocks of the various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments of the present invention in which data representing an image is generated, but a viewable image is not. Therefore, as used herein the term "image" broadly refers to both viewable images and data representing a viewable image. However, many embodiments generate, or are configured to generate, at least one viewable image.

Described herein are exemplary imaging systems and methods that enable an operator to position a narrow field-of-view camera at a first imaging position to acquire a first set of imaging information of a first object of interest, position the narrow field-of-view camera at a second imaging position to acquire a second set of imaging information of a second object of interest, determine emission counts for the first and second sets of imaging information, and utilize the determined emission counts to generate a value that indicates a probability of a successful medical procedure being performed on the subject.

Various embodiments may be implemented in different types of imaging systems, such as NM imaging systems having different arrangements and configurations of gamma cameras, for example, different types of SPECT systems. For example, various embodiments provide Cadmium Zinc Telluride (CdZnTe or CZT) SPECT cameras that provide increased resolution sampling of a narrow field of view (FOV). It should be noted that the various embodiments are not limited to CZT SPECT cameras and other imaging detectors, for example, other gamma cameras may embody the various embodiments, including detectors formed from different materials, such as Sodium Iodide (NaI), among others. Additionally, the various embodiments may be implemented in connection with other types of NM imaging systems, such as Positron Emission Tomography (PET) systems, as well as with dual-modality imaging systems.

An NM imaging system 10 may be provided as illustrated in FIG. 1 having an NM camera 20 configured as a SPECT detector housing 22. It should be noted that the various embodiments are not limited to the NM imaging system 10 having a single camera or detector housing 22 operable to perform SPECT imaging. For example, the NM imaging system 10 may include one or more additional cameras or detector housings 22 (one additional detector housing 22 is shown in dashed lines). An object, such as a patient 26, is positioned in proximity to the one or more detector housings 22 for imaging. It should be noted that one or more detector modules 24 within the detector housing 22 in various embodiments, may be aimed such that the detector modules 24 share the same FOV. It also should be noted that the detector modules 24 may be arranged in an array, such as in one row, two rows or more. For example, the detector modules 24 may be arranged in an array such that three rows each having nine detector modules 24 are provided.

It should be noted that number of detector housings 22 may be greater than two, for example three or more and the number of detector modules 24 may be greater or fewer. In a multi-detector camera, the position of the detector housings 22 may be, for example, substantially at 90 degrees to each other or in different configurations as known in the art.

In one embodiment, the detector modules 24 are formed from pixelated detector elements that may operate, for example, in an event counting mode and may be configured to acquire SPECT image data. The detector modules 24 may be formed from different materials, particularly semiconductor materials, such as CZT, cadmium telluride (CdTe), and silicon (Si), among others. In various embodiments, the plurality of detector modules 24 each includes detector elements having a plurality of pixels. However, it should be noted that the various embodiments are not limited to a particular type or configuration of detectors, and any suitable imaging detector may be used.

The detector modules 24 include pinhole collimation formed from pinhole collimators 28 (shown more clearly in FIG. 2) and coupled to a detecting face of the detector modules 24. The collimators 28 in some embodiments define a multi-pinhole collimator arrangement. Thus, in various embodiments, each of the pinhole collimators 28 has a pinhole opening 30 extending therethrough.

Figure 2:
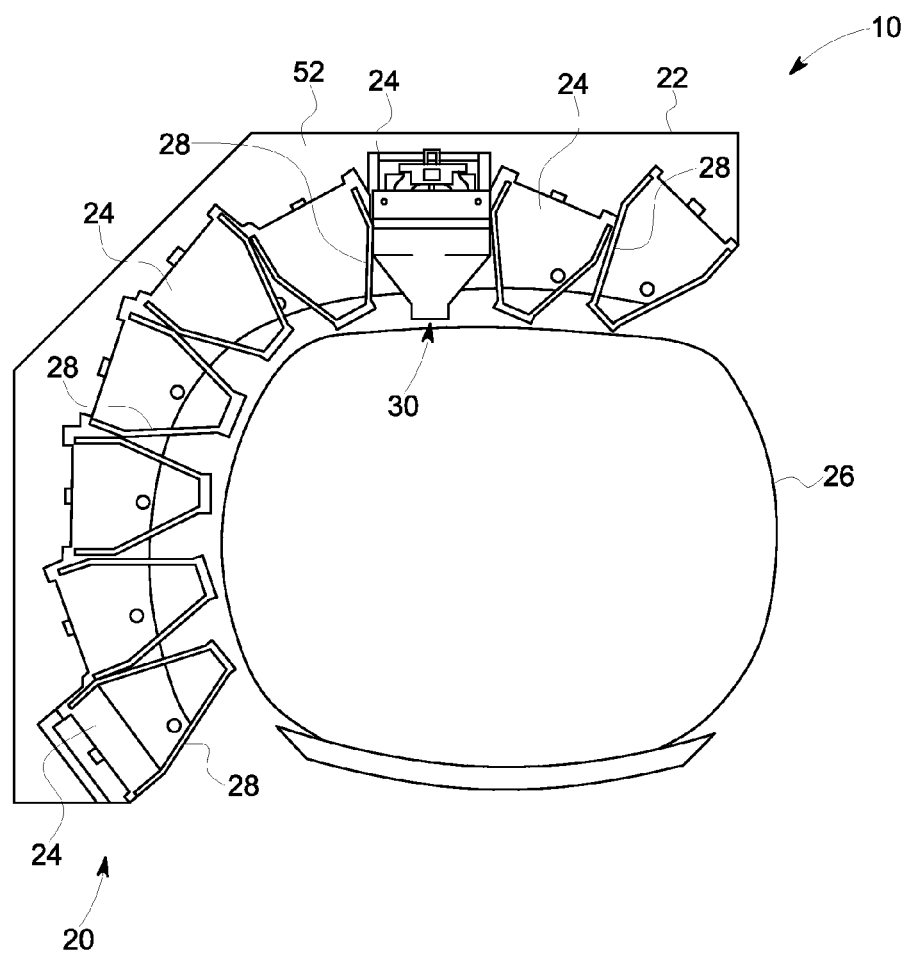
FIG. 2 is a diagram illustrating detector modules formed in accordance with various embodiments.

The detector housings 22 may be provided in different configurations, for example, in single planar imaging mode (illustrated in FIG. 1), a two detector housing 22 "L" mode configuration, multiple detector housings 22 configured along an arc (as shown in FIG. 2) an "H" mode configuration, or a three headed camera configuration, among others. Additionally, a gantry (not shown) supporting the detector housings 22 may be configured in different shapes, for example, as a "C" and the detector housings 22 may be arranged in different configurations.

The imaging system 10 also includes a detector controller 32 that operates to control the movement of the detector housings 22 about the patient 26. For example, the detector controller 32 may control movement of the detector housings 22, such as to rotate the detector housings 22 around the patient 26, and which may also include moving the detector housings closer or farther from the patient 26 and pivoting the detector housings 22.

The imaging system 10 also includes an image reconstruction module 34 configured to generate images from acquired image information 36 received from the detector housings 22. For example, the image reconstruction module 34 may operate using NM image reconstruction techniques, such as SPECT image reconstruction techniques to generate SPECT images of the patient 26, which may include an object of interest, such as the heart 38, the sternum 40, or the mediastinum 42 of the patient.

The image reconstruction module 34 may be implemented in connection with or on a processor 44 (e.g., workstation) that is coupled to the imaging system 10. In some embodiments, the image reconstruction module 34 may be implemented as a module or device that is coupled to or installed in the processor 44. Accordingly, the image reconstruction module 34 may be implemented in software, hardware or a combination thereof. In one embodiment, image reconstruction may be performed on a remote workstation (e.g., a viewing and processing terminal) having the processing components and not at the imaging scanner.

The image information 36 received by the processor 44 may be stored for a short term (e.g., during processing) or for a long term (e.g., for later offline retrieval) in a memory 46. The memory 46 may be any type of data storage device, which may also store different types of information. The memory 46 may be separate from or form part of the processor 44. A user input 48, which may include a user interface selection device, such as a computer mouse, trackball, touch screen, voice recognition, gesture detection and/or keyboard is also provided to receive a user input.

Thus, during operation, the output from the detector modules 24, which includes the image information 36, such as projection data from a plurality of detectors or gantry angles is transmitted to the processor 44 and the image reconstruction module 34 for reconstruction and formation of one or more images that may be displayed on a display 50. It should be noted that any suitable reconstruction method may be used.

In one embodiment, and with reference to FIG. 2, the detector modules 24 define a SPECT detector, which is provided in a multi-gamma camera, multi-pinhole detector arrangement. In the illustrated embodiment, the detector modules 24 are arranged and supported on a support structure 52 (e.g., a scanner gantry) in a generally curved or arcuate configuration in a generally or semi-arc shape or L-shaped arrangement similar to an L-mode of operation. The detector modules 24 may be arranged to provide, for example, organ specific imaging such that each of the detector modules 24 is fixed on the support structure 52. However, the detector modules 24 may be configured for other types of organ specific imaging or for general purpose imaging, and may be configured to be positionable, such that a field of view of the detector modules 24 can be adjusted during an exam or between exams.

It should be noted that one or more of the detector modules 24 may be positioned and oriented (e.g., angled) to focus on a region of interest, such as an organ of the patient 26 (e.g., heart, mediastinum, sternum, etc.). For example, for cardiac imaging, the detector modules 24 are positioned and oriented to focus on a single location that may include for example, the heart 38, the sternum 40, or the mediastinum of the patient 26. Thus, one or more of the detector modules 24 may be angled differently to focus on the area of interest.

Figure 3:
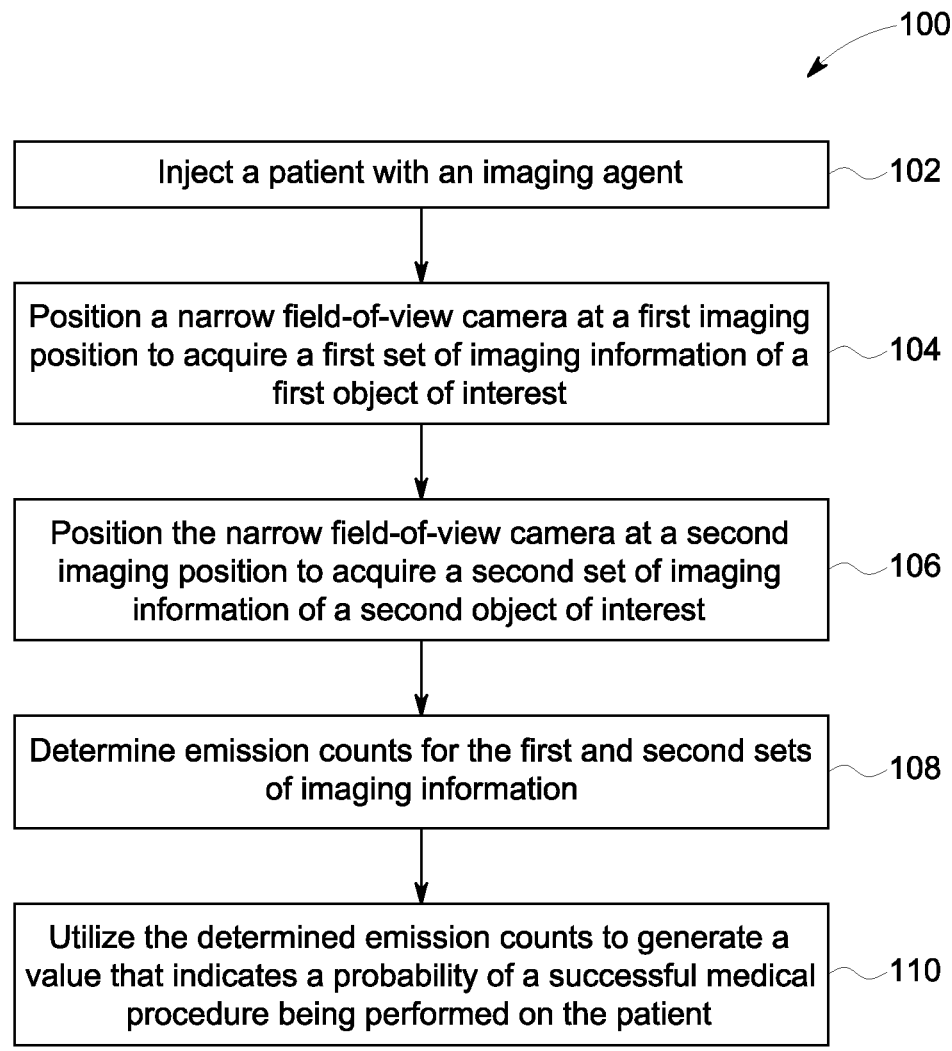
FIG. 3 is a flowchart of a method for performing an imaging scan of a subject in accordance with various embodiments.

FIG. 3 is a flowchart illustrating an exemplary method 100 for performing an imaging scan of a patient, such as for example, the patient 26. At 102, a patient, such as for example the patient 26 is injected with an imaging agent. The term "imaging agent" as used herein includes any and all radiopharmaceutical (RP) agents and contrast agents used in connection with diagnostic imaging and/or therapeutic procedures. In various embodiments, the imaging agent is iodine-131-meta-iodobenzylguanidine (mIBG) which is utilized to perform a mIBG study of the patient 26.

In various other embodiments, the imaging agent may represent a perfusion agent. The imaging agent may be, among other things, an imaging agent adapted for use in an NM system, such as the NM imaging system 10. By way of example only, the imaging agent may be Myoview™, Fluorodeoxyglucose (FDG), $^{18}$F-Flourobenzyl Triphenyl Phosphonium ($^{18}$F-FBnTP), $^{18}$F-Flouroacetate, $^{18}$F-labled myocardial perfusion tracers, Tc-ECD, Tc-HMPAO, N-13 ammonia, Envision N-13H3, $^{99m}$-Technitium ligands, Xenon-133, Neuroreceptor ligands, etc.), $^{18}$F-fluoromisonidazole, $^{201}$Thallium, $^{99m}$Technetium sestamibi, and $^{82}$Rubidium, among others. It should be realized that although various embodiments are described herein with respect to performing a mIBG study of the heart, that the methods system described herein may be utilized to image any organ or structure within the patient 26. Accordingly, the imaging agent injected into the patient 26 is selected based on the type of study being implemented.

Figure 4:
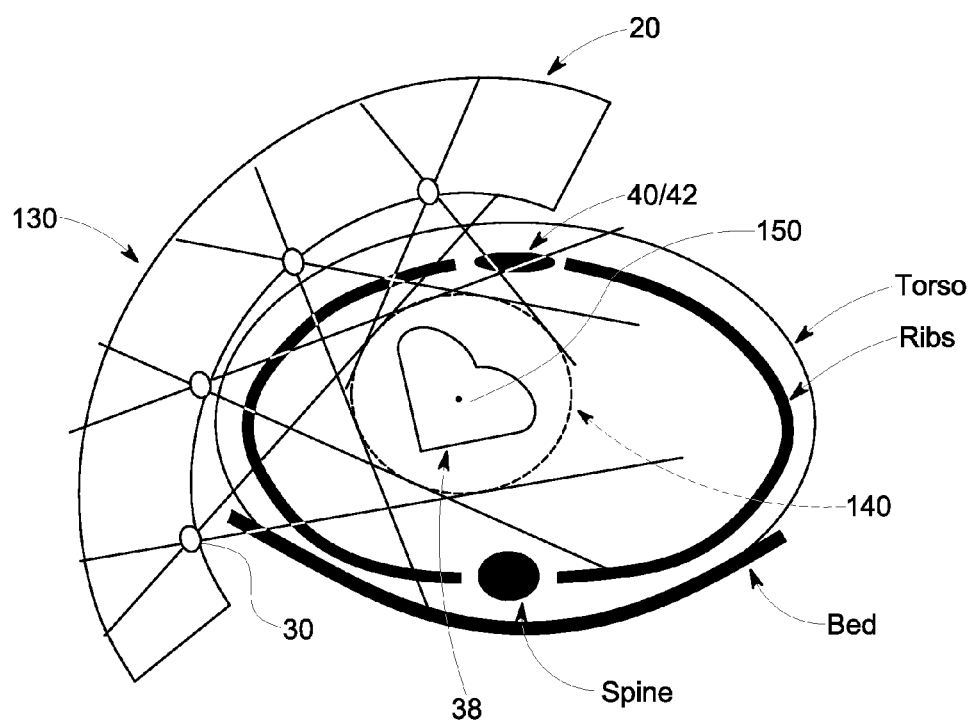
FIG. 4 is a diagram illustrating a first position of a nuclear camera in accordance with various embodiments.

Referring again to FIG. 3, at 104, a narrow field-of-view (FOV) camera, such as the NM camera 20, is positioned at a first imaging position to acquire a first set 120 of imaging information (shown in FIG. 1) of a first object of interest. The NM camera 20 may be positioned by manually and/or automatically moving the NM camera toward or away from the patient 26. Accordingly, the NM camera 20 may be moved or translated in three directions, along an x-axis, a y-axis, or z-axis, to position the NM camera 20 to image the heart 38. Moreover, in various embodiments, the detector modules 24 may be translated, rotated, or adjusted to image the heart 38. In one embodiment, a narrow FOV camera means an NM camera wherein the FOV is set to small enough to encompass substantially only the heart 38, the sternum 40, or the mediastinum 42. More specifically, as discussed above, when an NM camera 20 is operated with a narrow FOV, the sensitivity and possibly also the resolution of the NM camera 20 is significantly increased as compared to when the NM camera 20 is operated with a wide FOV. Thus, the imaging information 36, e.g. the emission counts, acquired at a narrow FOV has an improved accuracy as compared to a wide FOV NM camera. Thus, in various embodiments, the FOV of the NM camera 20 is set narrow enough that the FOV does not encompass both the heart and the sternum in the same FOV. In various embodiments, and as shown in FIG. 4, the first object of interest is the heart 38. Thus, in operation, the NM camera 20 is initially positioned at a first imaging position 130 to acquire imaging information 120 of the heart 38 within a narrow FOV 140. Thus, a focal point 150 of the NM camera 20 is centered within the heart 38.

In various embodiments, the NM camera 20 may be positioned to image the heart 38 using, for example, a persistence image. A persistence image is an image that depicts the decay of the imaging agent injected into the patient 26, and is not a reconstructed image. Accordingly, a plurality of persistence images may be utilized to depict the decay of the imaging agent injected over the previous few seconds. Accordingly, in various embodiments, the operator may view the persistence images to enable the operator to position the NM camera at the first imaging position 130. Moreover, the operator may view the persistence images to enable the operator to position the NM camera at the second imaging position 132, as described below.

Figure 5:
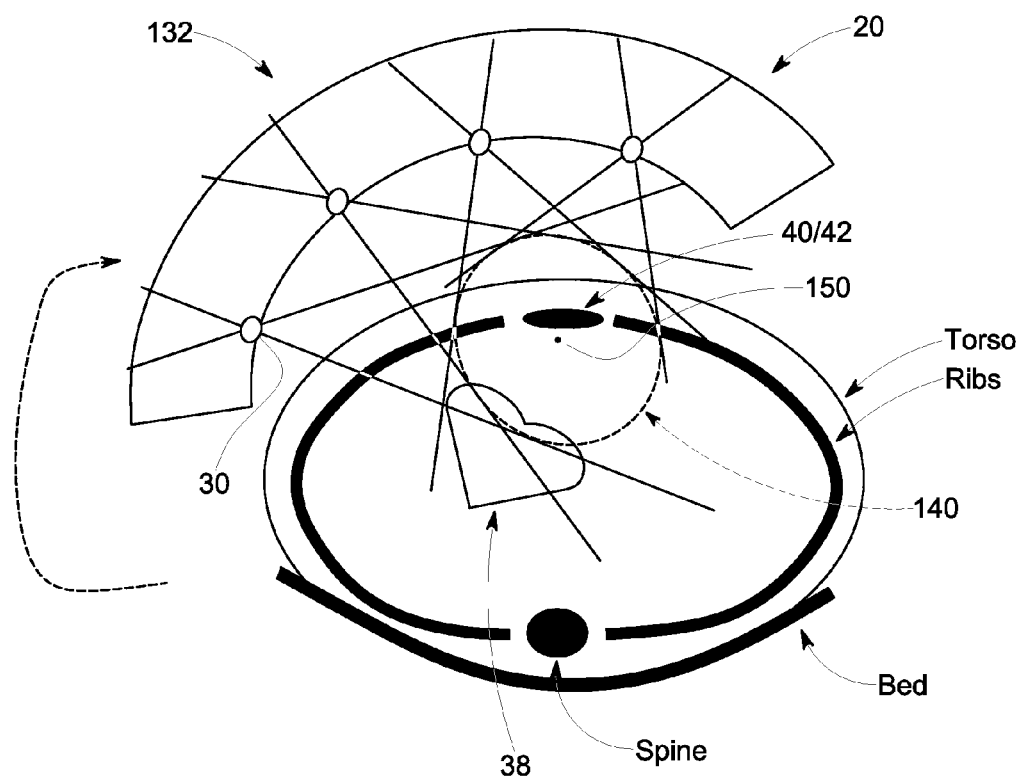
FIG. 5 is a diagram illustrating a second position of the nuclear camera in accordance with various embodiments.

Referring again to FIG. 3, at 106 the NM camera 20 is positioned at a second imaging position to acquire a second set of imaging information of a second object of interest. In various embodiments, and as shown in FIG. 5, the second object of interest is either the sternum 40 or the mediastinum 42. Thus, in one embodiment, the NM camera 20 is subsequently positioned, by translating or moving the NM camera 20 and/or the detector modules 24, to a second imaging position 132 to acquire a second set of imaging information 122 of either the sternum 40 or the mediastinum 42. Thus, the FOV 140 of the NM camera 20 is sized to encompass substantially only the sternum 40 or the mediastinum 42 and the focal point 150 of the NM camera 20 is approximately centered within the sternum 40 or the mediastinum 42. Optionally, repositioning may include maintaining the NM camera stationary and moving at least some of the detector modules 24 such that the FOV of the NM camera is moved to the second imaging position.

It should be realized that while various embodiments describe the NM camera 20 positioned to acquire information of the heart 38 and then repositioned to acquire information of the mediastinum 42, in other embodiments, the NM camera 20 may be positioned to initially acquire information of the mediastinum 42 and then repositioned to acquire information of the heart 38. For example, to place and/or dismount the patient 26 in the camera, the camera 10 may be moved away from the patient 26 (or the bed 310 shown in FIG. 8) which may be raised or lowered to allow patient placement and discharge. During the time that the camera approaches (or retracts) from the patent, the FOV of the camera may be directed to the second organ, thus allowing the camera 10 to acquire information during a time period that is typically wasted during a conventional image acquisition procedure.

Referring again to FIG. 3, at 108 the emission counts for the first and second sets of imaging information 120,122 are determined. More specifically, in operation, the patient is initially injected with the imaging agent at 102 as discussed above. As the imaging agent decays the imaging agent emits photons that are detected and counted by the NM camera 20. Accordingly, the emission photons counted by the NM camera 20 at the first imaging position 130 represent the total counts received for the uptake of the imaging agent in the heart 38. Moreover, the emission photons counted by the NM camera 20 at the second imaging position 132 represent the total counts received for the uptake of the imaging agent in, for example, the mediastinum 42. In various embodiments, the emission counts may be determined by reconstructing a three-dimensional (3D) image of the heart 38 and a 3D image of the mediastinum 42. The two 3D images may be normalized to enable the user to compare the concentration levels in both the heart 38 and the mediastinum 42 concurrently.

At 110, the emission counts determined for the heart 38 and the mediastinum 42 are utilized to generate a value that indicates a probability of a successful medical procedure being performed on the patient. More specifically, a mIBG study is useful to evaluate various medical conditions, such as for example, congestive heart failure. Moreover, mIBG studies are also useful in determining if a defibrillator may be implanted into a patient.

Accordingly, at 110, the emission counts determined for the heart 38 and the mediastinum 42 are utilized to generate a value that indicates a probability of a successful medical procedure, such as for example, defibrillator implantation, being performed on the patient. In various embodiments, the value generated at 110 is a heart-to-mediastinum ratio (H/M). Accordingly, at 110, the H/M is determined by calculating a ratio of the total counts of the heart 38 and the total counts of mediastinum 42 over the same time period. The total counts for the heart 38 and the total counts of mediastinum 42 are then utilized to generate the H/M ratio. The H/M ratio is then compared to a predetermined value that indicates the probability of the patient 26 undergoing a successful medical procedure. In various embodiments, the total heart counts and the total mediastinum counts may be calculated using the processor 44. Moreover, the H/M ratio may be calculated and compared to the predetermined value to generate the probability that the patient will undergo the successful medical procedure.

Figure 6:
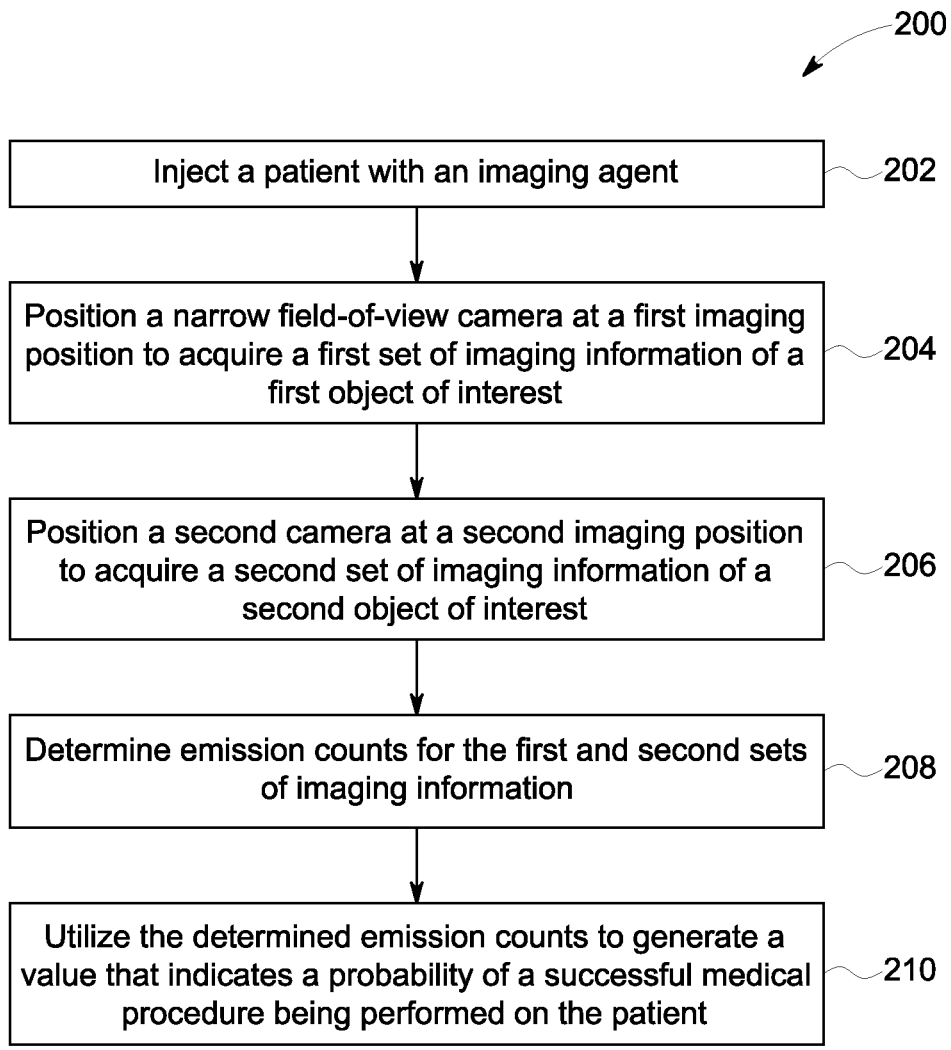
FIG. 6 is a flowchart of another method for performing an imaging scan of a subject in accordance with various embodiments.

FIG. 6 is a flowchart of another exemplary method 200 for performing an imaging scan of a patient, such as for example, patient 26. At 202, a patient, such as for example the patient 26 is injected with an imaging agent.

Figure 7:
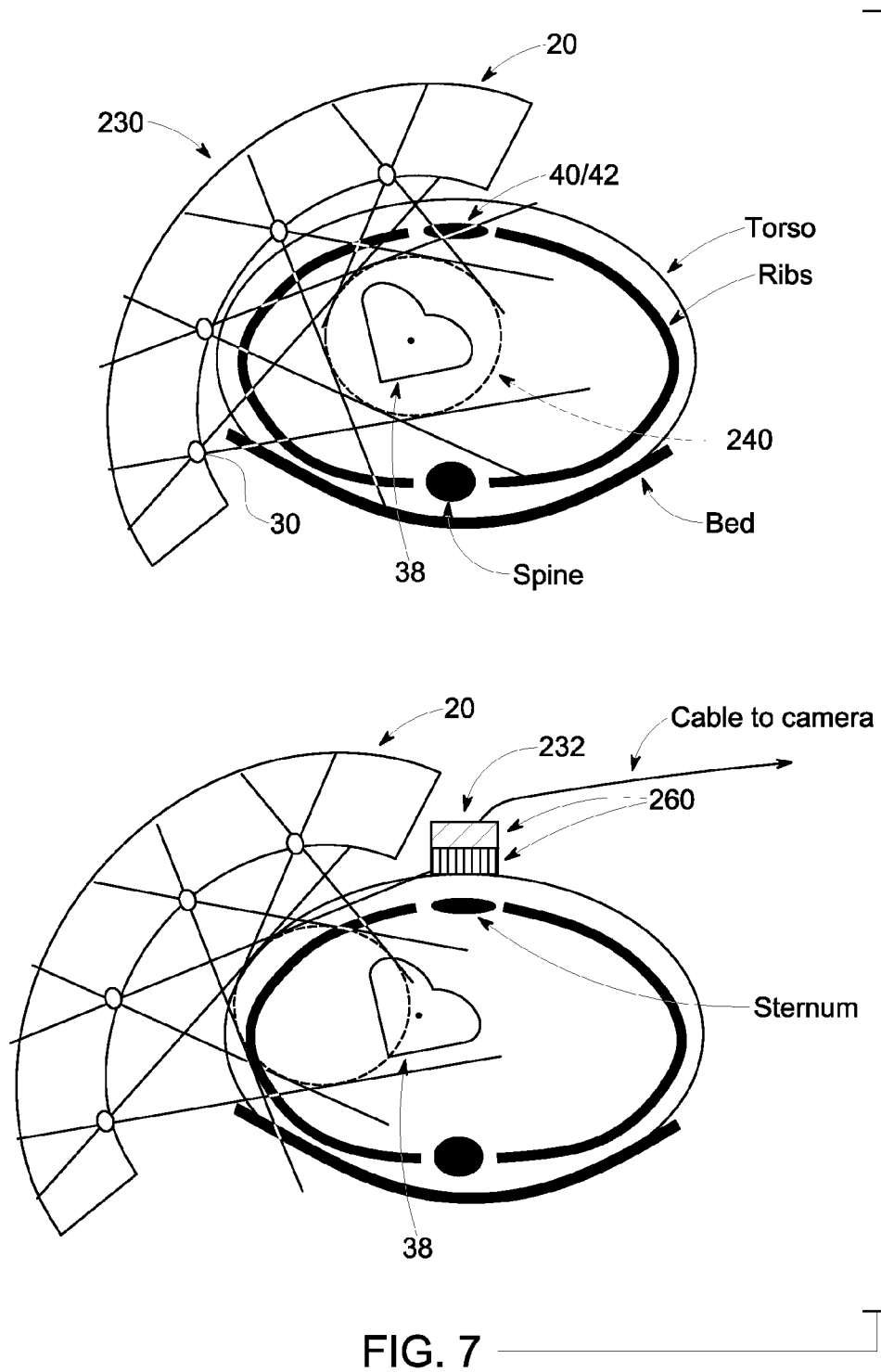
FIG. 7 is a diagram illustrating nuclear camera positions in accordance with various embodiments.

At 204, a narrow field-of-view (FOV) camera, such as the NM camera 20, is positioned at a first imaging position to acquire a first set 220 of imaging information (shown in FIG. 1) of a first object of interest. In various embodiments, and as shown in FIG. 7, the first object of interest is the heart 38. Thus, in operation, the NM camera 20 is initially positioned at the first imaging position 230, such that the heart 38 is within the narrow FOV 240, to acquire imaging information 220 of the heart 38. In various embodiments, the NM camera 20 may be positioned to image the heart 38 using, for example, a persistence image as described above.

Referring again to FIG. 7, at 206 the NM camera 20 is positioned away from the patient 26 and a second NM camera 260 is positioned at a second imaging position to acquire a second set of imaging information of a second object of interest. In various embodiments, and as shown in FIG. 7, the second object of interest is either the sternum 40 or the mediastinum 42. Thus, in operation, the second NM camera is subsequently positioned at a second imaging position 232 to acquire imaging information 222 of either the sternum 40 or the mediastinum 42. Thus, the FOV 140 of the NM camera 260 is sized to encompass substantially the sternum 40 or the mediastinum 42 and a focal point 250 of the camera 260 is centered within the sternum 40 or the mediastinum 42. In various embodiments, the NM camera 260 may be embodied as a CZT camera having a plurality of pinhole collimators. In various other embodiments, the NM camera 260 may have parallel hole collimators, converging collimators, or diverging collimators. Moreover, in various embodiments, the NM camera 260 may be a handheld camera that is manually positioned by the operator to acquire the imaging information 222 of the mediastinum 42.

In various embodiments, utilizing both the NN camera 20 and the NM camera 260 enables the operator to acquire the emission counts for the heart 38 concurrently with acquiring the emission counts for the mediastinum 42. It should also be realized that while various embodiments describe the NM camera 20 positioned to acquire information of the heart 38 and the NM camera 260 being utilized to acquire information of the mediastinum 42, in other embodiments, the NM camera 20 may be positioned to initially acquire information of the mediastinum 42 and then repositioned to acquire information of the heart 38.

Referring again to FIG. 7, at 208 the emission counts for the first and second sets of imaging information 220,222 of imaging information are determined as described above. At 210, the emission counts determined for the heart 38 and the mediastinum 42 are utilized to the H/M value as described above.

Various embodiments described herein provide a method and/or system for automatically generating a value that indicates a probability of a successful medical procedure being performed on the subject. A technical effect of at least one embodiment is to generate a more accurate H/M ratio to assist a physician in determining whether a patient will have a positive outcome to a defibrillator implantation procedure.

Figure 8:
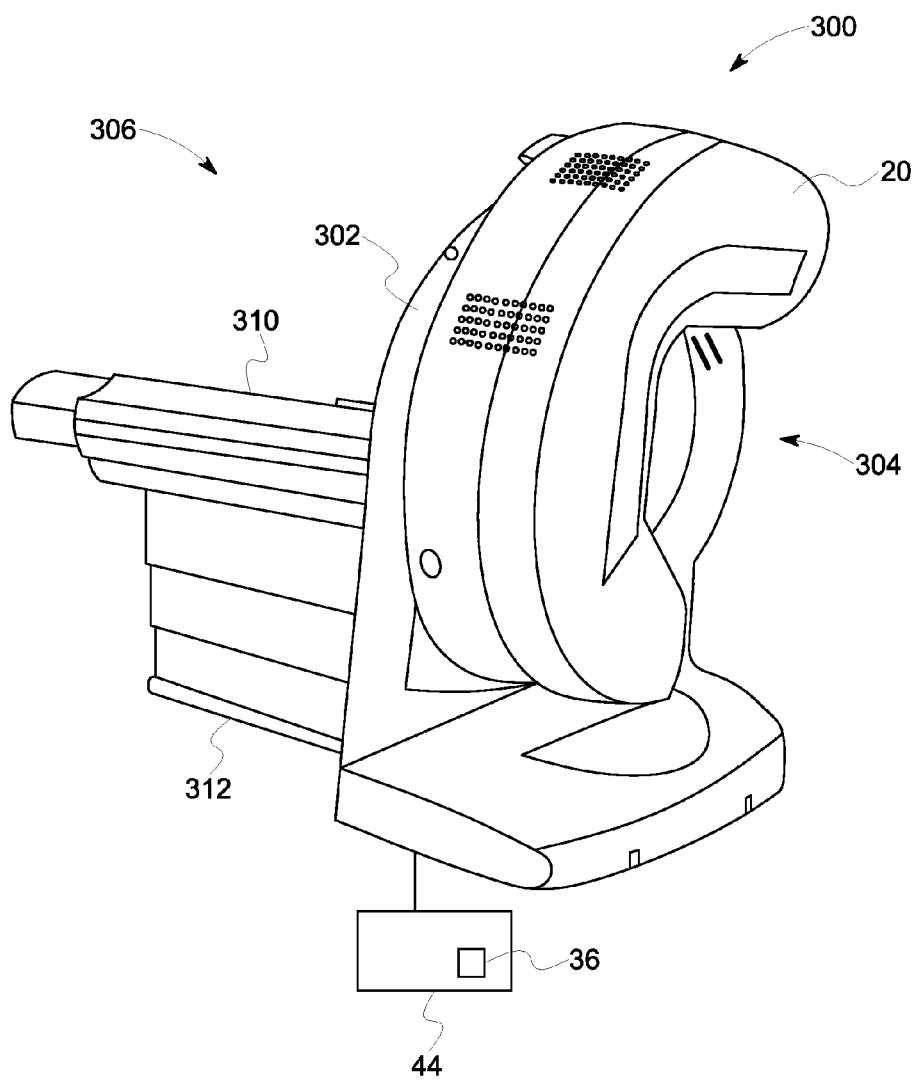
FIG. 8 is a perspective view of a Nuclear Medicine (NM) imaging system formed in accordance with various embodiments.

The various embodiments may be implemented in connection with any imaging system. For example, FIG. 8 is a perspective view of an exemplary imaging system 300 that may be utilized to implement the various methods described herein. The system 300 includes a gantry 302 having a gantry central bore 304. The gantry 302 is configured to support one or more NM radiation detectors, which may be configured as CZT imaging modules, for example, the NM camera 20 (shown in FIGS. 1 and 2) that is supported, for example, around approximately 180 degrees of the gantry 302. A patient table 306 may include the bed 310 slidingly coupled to a bed support system 312, which may be coupled directly to a floor or may be coupled to the gantry 302 through a base coupled to the gantry 302. The patient table 306 is configured to facilitate ingress and egress of a patient (such as the patient 26 shown in FIG. 1) into an examination position that is substantially aligned with the examination axis of the gantry central bore 302. The patient table 306 may also configured to facilitate up and down motion of bed 310. During an imaging scan, the patient table 306 may be controlled to move the patient 26 axially into and out of (as well as upward and downward within) the gantry central bore 304 to obtain event count information for the patient or a region of the patient. The operation and control of the imaging system 300 may be performed in any manner known in the art. It should be noted that the various embodiments may be implemented in connection with imaging systems that include stationary gantries or moving gantries. Additionally, the imaging system 300 may include the processor 44 having the imaging information 36 installed thereon.

Figure 9:
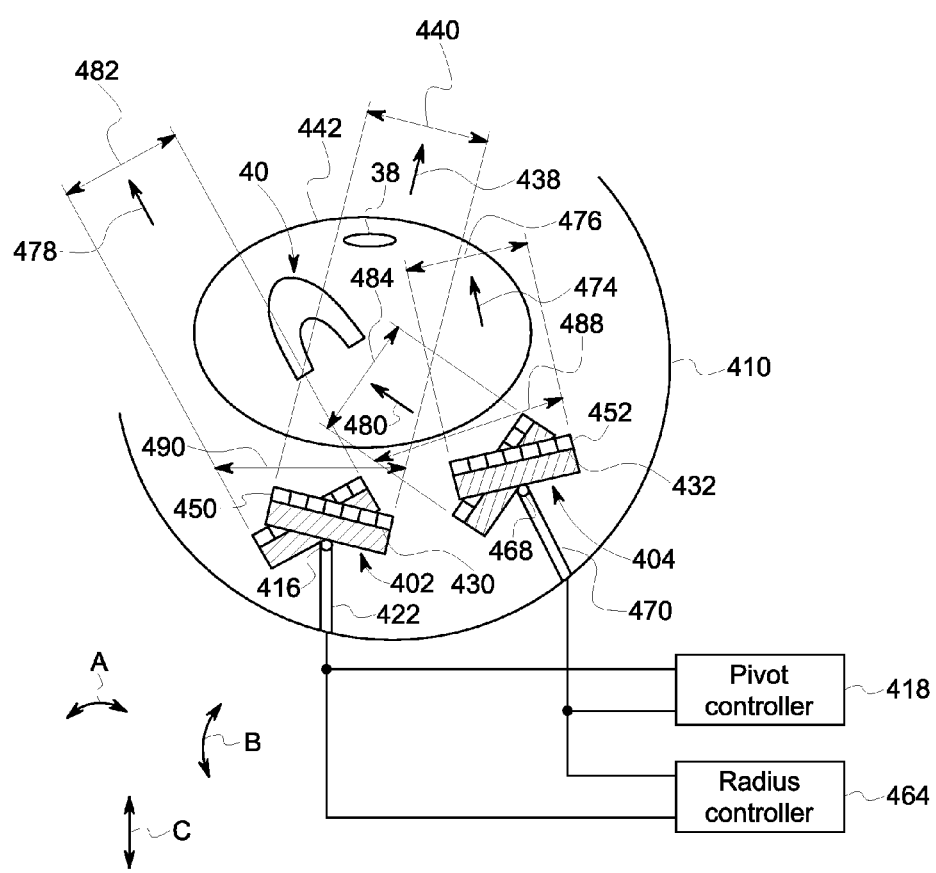
FIG. 9 illustrates a first and second imaging detector that may be utilized to implement the method of FIG. 3 in accordance with various embodiments.
Figure 10:
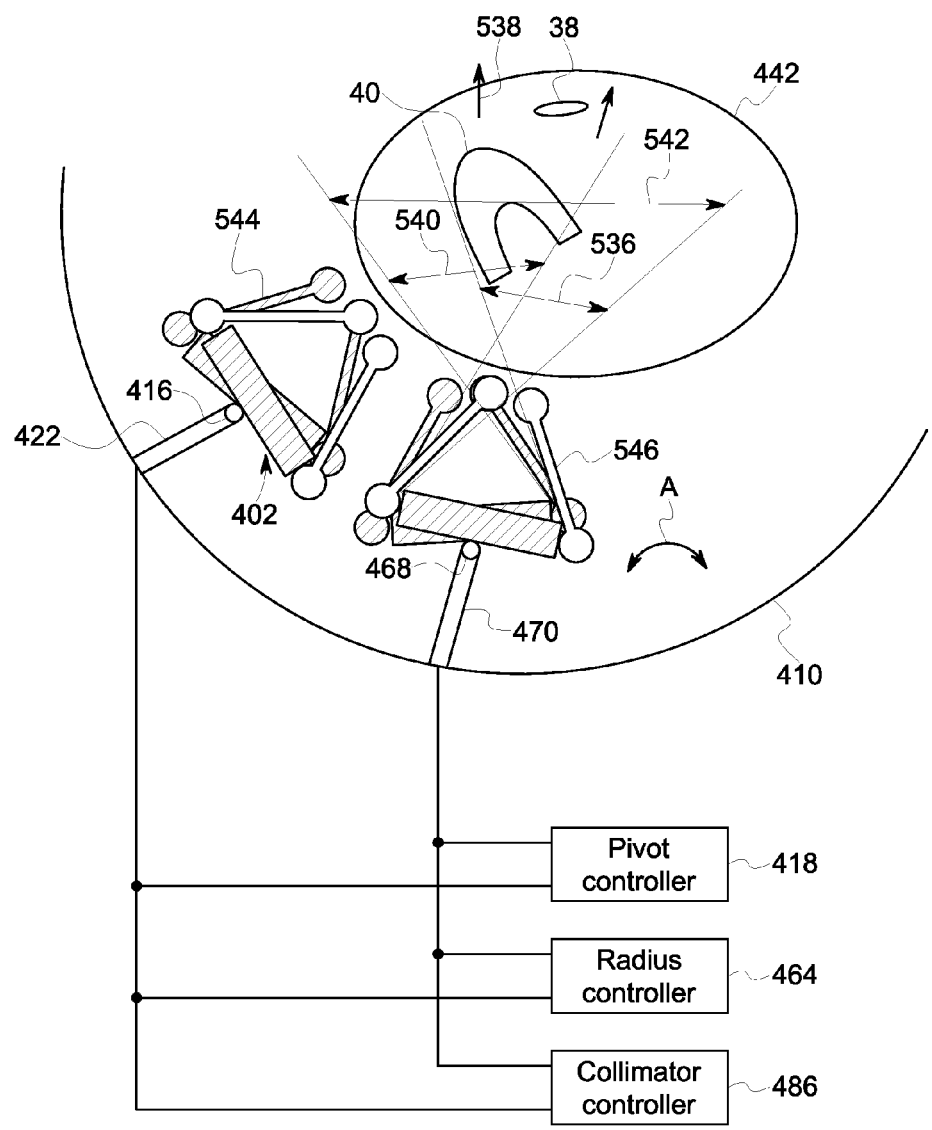
FIG. 10 illustrates the first and second imaging detectors of FIG. 9 with pinhole collimators attached thereto in accordance with various embodiments.

FIG. 9 illustrates a first and second imaging detector that may be utilized to implement the various methods described herein. FIG. 10 illustrates the first and second imaging detectors of FIG. 9 with pinhole collimators attached thereto in accordance with various embodiments. More specifically, the detectors of FIGS. 9 and 10 may be utilized with the imaging system shown in FIG. 8.

As shown in FIG. 9, the NM detectors may include a plurality of small imaging detectors mounted on a gantry, such as the gantry 302 shown in FIG. 8. As illustrated in FIG. 9, N is equal to two; however, it should be understood that two, three or more imaging detectors may be used. Each of the first through N imaging detectors 402 and 404 are smaller than a conventional imaging detector. A conventional imaging detector may be large enough to image most or all of a width of a patient's body at one time and may have a diameter of approximately 40 cm. In contrast, each of the first through N imaging detectors 402 and 404 may have dimensions of 4 cm to 20 cm and may be formed of cadmium zinc telluride (CZT) tiles. For example, each of the first through N imaging detectors 402 and 404 may be 8×8 cm in size and be composed of a plurality of CZT pixilated modules (not shown). For example, each module may be 4×4 cm in size and have 16×16=256 pixels. It should be understood that the first through N imaging detectors 402 and 404 may be different sizes and/or shapes with respect to each other, such as square, rectangular, circular or other shape. An actual field of view (FOV) of each of the first through N imaging detectors 402 and 404 may be directly proportional to the size and shape of the respective imaging detector.

Additional imaging detectors (not shown) may be positioned to form an arc or ring around a patient 442. Alternatively, more than one ring, arc or arch may be formed. By positioning multiple imaging detectors at multiple positions with respect to the patient 442, image data specific to a structure of interest within the patient 442 may be acquired more quickly compared to acquisitions using conventional large size detectors.

Optionally, imaging detectors may be arranged around the patient 442 in a closed pack formation. Optionally, imaging detectors may be arranged around the patient 442 in a plurality of axial locations. When imaging the sternum 38 or the heart 40, for example, two, three, four or more arches of imaging detectors may be used. Each arch may span 90 to 270 degrees around the patient 442, and together cover a substantial portion of the torso. For example, three arches configured using 8×8 cm sized imaging detectors would form a curved band of over 24 cm in width (taking into account some, preferably minimal, gap between imaging detectors).

Each of the N imaging detectors 402 and 404 has a radiation detection face 430 and 432, respectively, which is directed towards a structure of interest within the patient 442. The radiation detection faces 430 and 432 are each covered by a collimator 450 and 452, respectively. The actual FOV for each of the first through N imaging detectors 402 and 404 may be increased, decreased, or relatively unchanged by the type of collimator 450 and 452, such as pinhole, parallel-beam converging, diverging fan-beam, converging or diverging cone-beam, multi-bore, multi-bore converging, multi-bore converging Fan-Beam, multi-bore converging Cone-Beam, multi-bore diverging, or other type of collimator.

Optionally, multi-bore collimators may be constructed to be registered with pixels of a pixilated detector such as CZT pixilated detector. Registered collimation may increase spatial resolution by forcing photons going through one bore to be collected primarily by one pixel. Additionally, registered collimation may increase sensitivity and energy response of pixilated detectors as detector area near the edges of a pixel or in-between two adjacent pixels may have reduced sensitivity or decreased energy resolution or other performance degradation. Having collimator septa directly above the edges of pixels reduces the chance of photon impinging at these degraded-performance locations, without decreasing the overall probability of a photon passing through the collimator.

A controller unit, such as the controller 32 shown in FIG. 1 may control the movement and positioning of the imaging detectors 402 and 404, and the collimators 450 and 452. A range of motion during an acquisition or between images is set to keep the actual FOV of each of the first through N imaging detectors 402 and 404 directed towards or "aimed at" the structure of interest. The range of motion may be based on fixed or patient specific orbits, and small motions, such as detector "dither", may be used. Optionally, the amount or range of motion may be based on a preliminary image of the structure of interest. It should be noted that motion of one or more imaging detectors may be in directions other than strictly axially or radially, and optionally, motions in several motion directions may be combined to create the desired motion. Therefore, the term "motion controller" may be used to indicate a collective name for all motion controllers.

FIG. 9 illustrates pivoting motion used to increase the effective FOV of the first and second imaging detectors 402 and 404. It should be noted that detector motion or reorientation may also increase the sampling of the imaging data. Having a largely sampled dataset may improve reconstruction and may reduce artifacts. By pivoting the first and second imaging detectors 402 and 404, data can be collected from an area larger than the actual FOV. Each of the first through N imaging detectors 402 and 404 may be pivoted to change the direction from which the respective radiation detecting faces 430 and 432, respectively.

The first imaging detector 402 may be mounted on a pivot 416 and leg 422. The second imaging detector 404 may be mounted on a pivot 468 and a leg 470. Other pivoting mechanisms may be used. A pivot controller 418 may command the pivots 416 and 422 to move along arrow A, along arrow B (which is orthogonal to arrow A), or any position between the arrows A and B. The pivoting motion may be used together with one or more of the other movements previously discussed.

A pivot range for each of the first through N imaging detectors 402 and 404 may be determined. For example, when imaging a structure that is larger than the actual FOV of the first imaging detector 402, the pivot range may have a start point at one end wherein the FOV images one outer edge of the structure. Optionally, a predefined amount of surrounding tissue may be imaged. An end point of the pivot range may be set to image an opposite outer edge of the structure as well as a predefined amount of surrounding tissue. Therefore, a unique pivot range may be defined for each of the imaging detectors that may be specific to a particular scan.

Alternatively, one or more of the first through N imaging detectors 402 and 404 may be moved through a fixed, predetermined pivot range. A rate or speed of pivoting may also be predetermined, set by an operator, or determined based on the anatomy being scanned, size of the structure, level of radiation detected, and the like. It should be noted that rate of pivoting need not be constant throughout the pivot range, may be different for a different axis of pivoting, and may be different for different imaging detectors or throughout the duration of the acquisition. For example, the rate of pivoting may be higher during parts of the pivoting range wherein the first imaging detector 402 is aimed at the surrounding tissue. Thus, the first imaging detector 402 collects more data from the structure of interest than from the surrounding tissue.

Accordingly, in various embodiments, the first imaging detector 402 may acquire image data at a first position 438 corresponding to the start point of the pivot range. An actual FOV 440 of the first imaging detector 402 is dependent in part upon the collimator 450. The first imaging detector 402 is pivoted through the pivot range along the direction of arrow A to a second position 478 corresponding to the end point with actual FOV 482. An effective FOV 490 that is larger than either of the actual FOVs 438 and 478 is formed. The first imaging detector 402 may continuously acquire data while pivoting from the first position 438 to the second position 478. Alternatively, the first imaging detector 402 may acquire a series of images as the pivot controller 418 moves the imaging detector 402 through the pivot range 490. Alternatively, the pivot controller 418 may move the first imaging detector 402 to a predetermined number of positions within the pivot range 490, and the first imaging detector 402 acquires images at each of the positions. Although the example is illustrated in a single dimension, it should be understood that the effective field of view may be increased by pivoting the first imaging detector 402 in other directions.

The leg 422 and the leg 470 may be commanded by the radius controller 464 to move the first imaging detector 402 and/or the second imaging detector 404 towards and away from the patient 442 along arrow C. A distance 472 may thus be changed to increase or decrease the distance from the patient 442. The leg 422 may be piston driven, spring loaded, chain driven, or any other type of actuator. Alternatively, the leg 422 may be mounted on a segment (not shown) of the gantry 302, and thus the segment may also be driven in the direction of arrow C. The radius may be changed while acquiring data or between acquisitions, and may be used in combination with other motions. Anti-collision software and/or sensors (not shown) may also be used to ensure that the patient 442 does not collide with the first through N imaging detectors 402 and 404.

As shown in FIG. 9 the first and second imaging detectors 402 and 404 may use pivoting motion to increase an effective FOV to scan a structure of interest such as the heart 40 or the sternum 38. Although the first and second imaging detectors 402 and 404 are illustrated in one-dimension, as stated previously the radiation detecting faces 430 and 432 each have a two-dimensional FOV.

The collimators 450 and 452 are mounted proximate the radiation detecting faces 430 and 432. In this example, the collimators 450 and 452 are parallel beam collimators and therefore the actual FOVs of the first and second imaging detectors 402 and 404 are approximately equal to the actual or active size of the imaging detector.

The first imaging detector 402 is mounted on the pivot 416 which is interconnected to the gantry 302 by the leg 422 as discussed in FIG. 9. The second imaging detector 404 is similarly mounted on the pivot 468 which is interconnected to the gantry 302 by the leg 470. The pivot controller 418 and radius controller 464 controls the motion of the first and second imaging detectors 402 and 404 separately, and thus may move or swing the first imaging detector 402 in a direction different from the second imaging detector 404. The first and second imaging detectors 402 and 404 may also be moved at different rates with respect to each other as well as during the acquisition.

The first imaging detector 402 acquires a first image at the first position 438 which has the actual FOV 440. At the same time, the second imaging detector 404 acquires a first image at a first position 474 having an actual FOV 476. The first and second imaging detectors 402 and 404 are pivoted from the first positions 438 and 474 through Nth positions 478 and 480 which have actual FOVs 482 and 484, respectively. An effective FOV 488 is greater than the actual FOVs 476 and 484 of the first imaging detector 402 and an effective FOV 490 is greater than the actual FOVs 440 and 482 of the second imaging detector 404, and thus more data is acquired of the structure of interest and surrounding tissue.

Additional imaging detectors may be positioned around a portion or all of the patient 442 to acquire data of the structure of interest simultaneously with the first and second imaging detectors 402 and 404. The acquired data may be combined into a single composite dataset, and may be acquired in a shorter amount of time compared to a larger field of view detector.

FIG. 10 illustrates the first and second imaging detectors 402 and 404 of FIG. 9 with pinhole collimators 544 and 546, respectively, attached thereto. The pinhole collimators 544 and 546 illustrated have a single pinhole, and an actual FOV is defined by the pinhole geometry. The first and second imaging detectors 402 and 404 are mounted to the gantry 302 as discussed above and are interconnected with, and driven by, the pivot controller 418 and the radius controller 464. As discussed previously, an effective FOV which is larger than the actual FOV may be achieved by pivoting the first and second imaging detectors 402 and 404. The second imaging detector 404 will be discussed, although it should be understood that the first imaging detector 402, as well as any other imaging detectors installed on the gantry 302, may be operated in a similar fashion to simultaneously acquire patient data.

The second imaging detector 404 acquires a first image at a first position 534 which has an actual FOV 536. The pivot controller 418 pivots the second imaging detector 404 from the first position 534 toward the Nth position 538 along the arrow A. One or more images may be acquired between the first and Nth positions 534 and 538. The pivot controller 418 may stop the pivot motion during acquisition, or data may be acquired while the second imaging detector 404 is being pivoted. The FOV of the second imaging detector 404 is expanded from the actual FOV 536 to an effective FOV 542. As data is acquired from multiple positions around or proximate the patient 442, data of the structure of interest is collected faster and the acquisition time during which the patient 442 must remain without moving is shorter. A shorter data acquisition time also increases patient throughput and thus enables more efficient utilization of the imaging system, the clinic's space and operating personnel, and thus decreases the cost per image.

In addition, a collimator controller 486 may move the location of the pinhole of the pinhole collimator 546. Changing the position of the pinhole changes the actual FOV and thus the effective FOV. Alternatively, collimators having multiple pinholes which are configurable may be mounted to the first and second imaging detectors 402 and 404. The collimator controller 486 may control the position of the multiple pinholes for each multi-pinhole collimator separately. It should be noted that motion of the first and second detectors 402 and 404 relative to a stationary pinhole also causes the FOV to change and/or move. Additionally, changing the distance between the collimator or the pinhole(s) of the collimator and the detector changes the size of the FOV.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as an optical disk drive, solid state disk drive (e.g., flash RAM), and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for performing an imaging scan of a subject, said method comprising:

positioning a narrow field-of-view camera at a first imaging position to acquire a first set of imaging information of a first object of interest;

re-positioning the narrow field-of-view camera at a second imaging position that is different from the first imaging position to acquire a second set of imaging information of a second object of interest that is different from the first object of interest, wherein the second imaging position has a different field of view than the first imaging position;

determining corresponding emission counts separately for the first and second sets of imaging information;

calculating a ratio of the emission count for the first set of imaging information to the emission count for the second set of imaging information;

comparing the ratio to a predetermined threshold value; and determining that a medical procedure has a higher likelihood of success if the ratio is larger than the predetermined threshold value, and that the medical procedure has a lower likelihood of success if the ratio is lower than the predetermined threshold value.

2. The method of claim 1, wherein the narrow field of view camera comprises a plurality of pinhole cameras.

3. The method of claim 1, wherein the narrow field of view camera comprises a nuclear medicine camera including a plurality of detector modules mounted on a single housing, each of the detector modules including a pinhole collimator.

4. The method of claim 1, further comprising injecting the subject with a metaiodobenzylguanidine (mIBG) radiotracer.

5. The method of claim 4, wherein the mIBG radiotracer is radioiodinated.

6. The method of claim 1, wherein the first object is a heart, the second object is a mediastinum, and the value is a heart-to-mediastinum ratio.

7. The method of claim 1, wherein the medical procedure comprises a defibrillator implantation procedure.

8. The method of claim 1, wherein the second object is outside of a field of view of the narrow field-of-view camera when the narrow field-of-view camera is in the first imaging position, and the first object is outside the field of view of the narrow field-of-view camera when the narrow field-of-view camera is in the second imaging position.

9. The method of claim 1, further comprising acquiring at least one persistence image and determining at least one of the first imaging position or the second imaging position using the at least one persistence image.

10. A non-transitory computer readable medium encoded with a program programmed to instruct a computer to:

acquire a first set of imaging information of a first object of interest using a narrow field-of-view camera positioned at a first imaging position;

re-position the narrow field-of-view camera from the first imaging position to a second imaging position that is different from the first imaging position to acquire a second set of imaging information of a second object of interest that is different from the first object of interest using the narrow field-of-view camera positioned at a second imaging position, wherein the second imaging position has a different field of view than the first imaging position;

determine corresponding emission counts separately for the first and second sets of imaging information;

calculate a ratio of the emission count for the first set of imaging information to the emission count for the second set of imaging information;

compare the ratio to a predetermined threshold value; and determine that a medical procedure has a higher likelihood of success if the ratio is larger than the predetermined threshold value, and that the medical procedure has a lower likelihood of success if the ratio is lower than the predetermined threshold value.

11. The non-transitory computer readable medium of claim 10 wherein the narrow field of view camera comprises a plurality of pinhole cameras.

12. The non-transitory computer readable medium of claim 10, wherein the narrow field of view camera comprises a nuclear medicine camera including a plurality of detector modules mounted on a single housing, each of the detector modules including a pinhole collimator.

13. The non-transitory computer readable medium of claim 10, further programmed to instruct a computer to acquire the first and second sets of imaging information after the subject is injected with a metaiodobenzylguanidine (mIBG) radiotracer.

14. The non-transitory computer readable medium of claim 13, wherein the mIBG tracer is radioiodinated.

15. The non-transitory computer readable medium of claim 10, wherein the first object is a heart, the second object is a mediastinum, and the value is a heart-to-mediastinum ratio.

16. The non-transitory computer readable medium of claim 10, wherein the medical procedure comprises a defibrillator implantation procedure.

17. The non-transitory computer readable medium of claim 10, wherein the second object is outside of a field of view of the narrow field-of-view camera when the narrow field-of-view camera is in the first imaging position, and the first object is outside the field of view of the narrow field-of-view camera when the narrow field-of-view camera is in the second imaging position.

18. The non-transitory computer readable medium of claim 10, further programmed to instruct a computer to acquire at least one persistence image and to determine at least one of the first imaging position or the second imaging position using the at least one persistence image.

* * * * *